(12) United States Patent
Demierre

(10) Patent No.: US 9,310,305 B2
(45) Date of Patent: Apr. 12, 2016

(54) ENCODED MICROCARRIERS, ASSAY SYSTEM USING THEM AND METHOD FOR PERFORMING AN ASSAY

(75) Inventor: Nicolas Demierre, Châtel-St-Denis (CH)

(73) Assignee: MyCartis NV (BE)

( * ) Notice: Subject to any disclaimer, the term of this patent is extended or adjusted under 35 U.S.C. 154(b) by 108 days.

(21) Appl. No.: 13/980,721

(22) PCT Filed: Feb. 6, 2012

(86) PCT No.: PCT/CH2012/000032
§ 371 (c)(1),
(2), (4) Date: Jul. 19, 2013

(87) PCT Pub. No.: WO2012/106827
PCT Pub. Date: Aug. 16, 2012

(65) Prior Publication Data
US 2013/0302910 A1    Nov. 14, 2013

(30) Foreign Application Priority Data

Feb. 7, 2011    (EP) .................................... 11000970

(51) Int. Cl.
*G01N 33/543*    (2006.01)
*G01N 21/64*    (2006.01)
*B01L 3/00*    (2006.01)

(52) U.S. Cl.
CPC ...... *G01N 21/6486* (2013.01); *B01L 3/502761* (2013.01); *B01J 2219/005* (2013.01); *B01J 2219/0056* (2013.01); *B01J 2219/0074* (2013.01); *B01J 2219/00459* (2013.01); *B01J 2219/00558* (2013.01); *B01J 2219/00576* (2013.01); *B01J 2219/00725* (2013.01); *B01L 2200/0647* (2013.01); *B01L 2300/021* (2013.01); *B01L 2300/0832* (2013.01); *G01N 33/54313* (2013.01)

(58) Field of Classification Search
CPC ................. G01N 35/00732; B01J 2219/00497
See application file for complete search history.

(56) References Cited

U.S. PATENT DOCUMENTS

2003/0129654 A1 *  7/2003 Ravkin et al. .................. 435/7.1

FOREIGN PATENT DOCUMENTS

| EP | 1 464 700 | 10/2004 | ............ C12N 15/00 |
| GB | 2 404 918 | 2/2005 | ............... B01J 19/00 |
| WO | WO 00/63695 | 10/2000 | ........... G01N 33/532 |
| WO | WO2005/079544 | * 9/2005 | |
| WO | WO 2010/072011 | 7/2010 | ............... B01L 3/00 |

OTHER PUBLICATIONS

International Search Report for International Application No. PCT/CH2012/000032, May 7, 2012.

* cited by examiner

*Primary Examiner* — Melanie Y Brown
*Assistant Examiner* — Rebecca Martinez
(74) *Attorney, Agent, or Firm* — Kusner & Jaffe

(57) ABSTRACT

The present invention relates to an encoded microcarrier comprising a readable code attached to it for identification, said encoded microcarrier comprising a body having at least a detection surface to detect a chemical and/or biological reaction, the microcarrier further comprising at least a spacing element projecting from the body and shaped to ensure that, when the encoded microcarrier is laid on a flat plane with the detection surface facing said flat plane, a gap exists between said flat plane and the detection surface. The invention also relates to an assay device designed to use a plurality of said encoded microcarriers to perform assays. The invention relates finally to a method for monitoring a chemical or biological reaction.

15 Claims, 3 Drawing Sheets

ENCODED MICROCARRIERS, ASSAY SYSTEM USING THEM AND METHOD FOR PERFORMING AN ASSAY

FIELD OF THE INVENTION

The present invention relates to an encoded microcarrier, and more specifically to a microcarrier having spacing element, to an assay system, and to a method for performing a chemical and/or biological assay.

BACKGROUND OF THE INVENTION

Within the scope of the present invention, a microparticle or a microcarrier refer to any type of particles, respectively to any type of carriers, microscopic in size, typically with the largest dimension being from 100 nm to 300 micrometers, preferably from 1 µm to 200 µm.

According to the present invention, the term microcarrier refers to a microparticle functionalized, or designed to be functionalized, that is containing, or designed to contain, one or more ligands or functional units bound to the surface of the microcarriers or impregnated in its bulk. A large spectrum of chemical and biological molecules may be attached as ligands to a microcarrier. A microcarrier can have multiple functions and/or ligands. As used herein, the term functional unit is meant to define any species that modifies, attaches to, appends from, coats or is covalently or non-covalently bound to the surface of said microcarrier or impregnated in its bulk. These functions include all functions that are routinely used in high-throughput screening technology and diagnostics.

Any reference in this disclosure to a code of a microcarrier or of a microparticle includes codes written on the surface of said microcarrier, or of said microparticle, as well as codes written at an internal depth of the microcarrier or microparticle. Such codes and methods for writing codes are disclosed, for example, in the patent application WO 00/63695 which is herein incorporated by reference. In particular, all aspects of the patent application WO 00/63695 related to the codes and the methods for writing and reading are herein specifically incorporated by reference.

Drug discovery or screening and DNA sequencing commonly involve performing assays on very large numbers of compounds or molecules. These assays typically include, for instance, screening chemical libraries for compounds of interest or particular target molecules, or testing for chemical and biological interactions of interest between molecules. Those assays often require carrying out thousands of individual chemical and/or biological reactions.

A number of practical problems arise from the handling of such a large number of individual reactions. The most significant problem is probably the necessity to label and track each individual reaction.

One conventional method of tracking the identity of the reactions is achieved by physically separating each reaction in a microtiter plate. The use of microtiter plate, however, carries several disadvantages like, in particular, a physical limitation to the size of microtiter plate used, and thus to the number of different reactions that may be carried out on the plate.

In light of the limitations in the use of microarray, they are nowadays advantageously replaced by functionalized encoded microparticles to perform chemical and/or biological assays. Each functionalized encoded microparticle is provided with a code that uniquely identifies the particular l' ligand(s) bound to its surface. The use of such functionalized encoded microparticles allows for random processing, which means that thousands of uniquely functionalized encoded microparticles may all be mixed and subjected to an assay simultaneously. Examples of functionalized encoded microparticles are described in the international patent application WO 00/63695 and are illustrated in FIG. 1.

The international patent application WO 2010/072011 describes an assay device having at least a microfluidic channel which serves as a reaction chamber in which a plurality of functionalized encoded microparticles 1 (FIG. 1) can be packed. The microfluidic channel is provided with stopping means acting as filters that allow a liquid solution containing chemical and/or biological reagents to flow through while blocking the functionalized encoded microparticles 1 inside. The geometrical height of said microfluidic channels and the dimensions of said functionalized encoded microparticles 1 are chosen so that said microparticles are typically arranged in a monolayer arrangement inside each microfluidic channels preventing said microparticles 1 to overlap each other.

Those functionalized encoded microparticles 1 that show a favorable reaction of interest between their attached ligand(s) and the chemical and/or biological reagents flowing through may then have their code read, thereby leading to the identity of the ligand that produced the favorable reaction.

The term microfluidic channel refers to a closed channel, i.e. an elongated passage for fluids, with a cross-section microscopic in size, i.e. with the largest dimension of the cross-section being typically from about 1 to about 500 micrometers, preferably about 10 to about 300 micrometers. A microfluidic channel has a longitudinal direction, that is not necessarily a straight line, and that corresponds to the direction in which fluids are directed within the microfluidic channel, i.e. preferably essentially to the direction corresponding to the average speed vector of the fluid, assuming a laminar flow regime.

With the assay device described in WO 2010/072011, the detection of a reaction of interest can be based on continuous readout of the fluorescence intensity of each functionalized encoded microparticle 1 present in a microfluidic channel, as depicted in FIG. 6a. FIG. 6a clearly shows that it is difficult or even impossible to extract early quantitative information from the slopes at the origin when considering the intensity of each functionalized encoded microparticle 1 as a function of time. Therefore, the functionalized encoded microparticles 1 and the assay device described in WO 2010/072011 do not allow for a rapid quantification of reagent or ligand before an equilibrium state is reached, when the fluorescent signals saturate. Although the assay device of WO 2010/072011 decreases the time needed to reach equilibrium, in typical concentration values of analyte in the nano-molar range, ten to twenty minutes are still required, while lower concentration in the pico-molar range can take up to hours to be reached and serve for quantification. Moreover, the discrepancies in their fluorescent signals, in particular the diffusion pattern even after the equilibrium has been reached does not determine a quantitative information with a lower margin of error than about 15%.

The present invention aims to remedy all or part of the disadvantages mentioned above.

SUMMARY OF THE INVENTION

The present invention fulfills these objectives by providing an encoded microcarrier, comprising a readable code for identifying the microcarrier, said microcarrier comprising a body having at least a detection surface to detect a chemical and/or biological reaction, the microcarrier comprising at least a spacing element projecting from the body and shaped to ensure that, when the encoded microcarrier is laid on a flat plane with the detection surface facing said flat plane, a gap exists between said flat plane and this detection surface.

The invention also relates to an assay system comprising a plurality of encoded microcarriers according to the invention and further comprising an assay device having at least a microfluidic channel shaped to accommodate a plurality of said encoded microcarriers, said microfluidic channel having at least an observation wall through which an assay is monitorable, wherein said microfluidic channel and spacing elements of each encoded microcarrier are shaped to ensure that, when said encoded microcarrier is introduced in said microfluidic channel with said detection surface facing said observation wall, a gap exists between said detection surface and said observation wall to allow a circulation of fluid in said gap.

Furthermore, the invention concerns a method for performing a chemical and/or biological assay comprising a step of using at least an encoded microcarrier according to the invention, wherein a chemical and/or biological reaction is monitored on a detection surface of said encoded microcarrier.

Thus, at least one encoded microcarrier according to the invention can be used in an assay device having a microfluidic channel to perform chemical and/or biological assays in a rapid, multiplex and quantitative manner. The encoded microcarrier according to the invention allows early quantitation in a multiplex quantitative analysis, typically in the first few seconds of the assay, therefore significantly decreasing the duration (typically dividing by at least ten the duration) of a quantitative analysis performed with the functionalized encoded microparticles described in WO 2010/072011. It has also been discovered that an assay device according to the invention also requires much less encoded microcarriers to obtain a reliable quantitative analysis, in comparison to the quantity of required functionalized encoded microparticles of the prior art, therefore increasing the level of multiplexing and reducing readout time. When the encoded microcarrier is introduced in the microfluidic channel of the assay device with its detection surface facing the observation wall, a liquid solution containing the chemical and/or biological reagents used for the assays can flow in the gap between said detection surface and said observation wall generated by the spacing elements. The spacing elements permit to align the encoded microcarriers in the geometrical height of the microfluidic channel and therefore facilitate the flow of the liquid solution through the microfluidic channel.

The exact positioning of the functionalized encoded microparticles 1 of the prior art is not controlled during their packing into the microfluidic channel and some of them are in contact with one of the surfaces of the microfluidic channel, notably the observation wall. Such contacts prevent a convective flow to occur between the touching surfaces (one of which can be the detection surface) and restrict the mass transfers of reagents to a diffusive flow for those detection surfaces of functionalized encoded microparticles in contact with a surface of the microfluidic channel.

To the opposite, with the encoded microcarrier of the present invention, each spacing element prevents any contact between the detection surface and a wall of the microfluidic channel, forces a convective flow and avoids the reaction on the detection surface to be governed only by a diffusive flow. A particular wall of the microfluidic channel is for example an observation wall of an assay device.

According to an embodiment, when the encoded microcarrier is laid on a flat plane with the detection surface facing that flat plane, the contacting surface intended to be in contact with said flat plane represents less than 20% of the detection surface, preferably less than 15%, more preferably less than 7%. Thereby it is possible to promote a mass transfer with respect to diffusive flow. A particular flat plane is for example an observation wall of an assay device. When the encoded microcarrier lays on a flat plane with the detection surface facing that flat plane, the contacting surface intended to be in contact with said flat plane represents less than 20% of the portion of the detection surface facing said flat plane, preferably less than 15%, more preferably less than 7%.

According to a technical feature, the detection surface has at least an area wherein, when said microcarrier is laid on a flat plane with the detection surface facing said flat plane, each point of said area belongs to two different cross-sections of said encoded microcarrier which are perpendicular to each other and to said plane, said cross-sections being free of spacing element. This technical feature ensures that, when the microcarrier lays flat against said flat plane and is in a laminar flow essentially parallel to that flat plane, the orientation of the microcarrier around an axis normal to the flat plane does not significantly affect the flow in the gap. In other words, there is no preferred rotational orientation of the microcarrier with regard to the flow, which would change the efficacy of a reaction happening on the detection surface.

In an embodiment, said contacting surface is only formed by all the spacing elements. More preferably, the contacting surface consists in at least an end of the spacing element(s) distal from the detection surface. Such end is also termed a distal end.

In an embodiment, the contacting surface is distant from the detection surface.

In an embodiment, the encoded microcarrier comprises at least two, preferably at least three spacing elements designed so that, when the encoded microcarrier is laid on a flat plane, said at least two spacing elements face said flat plane.

According to an embodiment of the invention, the body has a cylindrical shape or a wafer shape.

In a preferred embodiment, the detection surface is substantially flat.

In an embodiment, at least a spacing element is integral with said body. In another embodiment, at least a spacing element is a separated part which is bound to the body.

According to an embodiment, when the encoded microcarrier is laid on a flat plane with a detection surface facing said flat plane, the greatest distance between said detection surface and said flat plane is greater than 5%, preferably greater than 10%, of the greatest height of the encoded microcarrier. Thereby the size of the cross-section of the gap between the detection surface and the flat plane is increased while the congestion created by the encoded microcarrier in a microfluidic channel is reduced to allow a laminar flow in said microfluidic channel. Such an increased size of the cross-section of the gap will increase the speed of the flow relative to the detection surface and therefore increase the chances of contact between molecules of interest in the fluid solution and the ligand(s) attached to the encoded microcarrier. It increases the assay sensitivity. Moreover, this ratio reduces the fluidic resistance of a liquid flowing through when said encoded microcarriers are loaded in a microfluidic channel. Reducing the microfluidic resistance means that the number of encoded microcarriers loaded in a given microfluidic channel during an assay can be increased, increasing therefore the level of multiplexing. It has been found that the encoded microcarrier of the invention preserves the integrity of the assay device during an assay.

In an embodiment, each spacing element protrudes from at least a detection surface.

In a preferred embodiment, each spacing element is shaped to ensure that, when the encoded microcarrier is laid on a flat plane with the detection surface facing said flat plane, said flat plane and said detection surface are substantially parallel to each other. Thereby the gap between the detection surface and said flat plane promote a laminar flow when the encoded microcarrier is loaded in a microfluidic channel. An encoded microcarrier, according to the invention, wherein the distance between said flat plane and the detection surface is constant promotes a laminar flow.

According to one possibility, each spacing element is located at the periphery of the detection surface.

The encoded microcarriers of the invention may be made from or comprise any material routinely used in high-throughput screening technology and diagnostics. Non-limiting examples of these materials include latex, polystyrene, cross-linked dextrans, polymethylstyrene, polycarbonate, polypropylene, cellulose, polyacrylamide, polydimethylacrylamide, fluorinated ethylene-propylene as well as materials commonly used in micro fabrication or micro milling such as glass, $SiO_2$, silicon, PMMA (polymethylmethacrylate), polysilicon, molubden, polyimide, gold, silver, aluminum, steel or other metals or epoxy-based photosensitive materials such as SU-8. The encoded microcarrier may be of any shapes and sizes. Preferably, the encoded microcarriers are made of silicon crystal.

In an embodiment, the encoded microcarrier of the invention is encoded in such a way that its function can be determined by reading the code.

In a preferred embodiment, the body of the encoded microcarrier of the invention has a form of a wafer. The term wafer means that the body of the encoded microcarrier has two essentially parallel and essentially flat major surfaces, one of which at least serves as a detection surface, and that its height between the two major surfaces is notably smaller (e.g. by at least a factor of two) than both its width and its length.

According to a technical feature, each major surface can have any shape; non limiting examples are a square, a rectangle, a circle, a triangle or a hexagon.

Thus, when encoded microcarriers with a body that has the form of a wafer are introduced in a microfluidic channel with a rectangular or close to rectangular section as described in patent application WO2010/072011, they have their two major surfaces essentially facing two major surfaces of the microfluidic channel, one of which is the observation wall, and they can be easily detected by optical means through the observation wall.

In another embodiment, the encoded microcarriers have magnetic properties. Thereby they can be immobilized within the microfluidic channel.

In an embodiment, the method according to the invention further comprises a step of introducing one or more encoded microcarriers in a microfluidic channel of an assay device according to the invention.

In a preferred embodiment, the method according to the invention further comprises a step of reading the attached code of said encoded microcarrier through said observation wall of the assay device.

In an embodiment, the method further comprising a step of reading the attached code of said encoded microcarrier through said observation wall of the assay device.

BRIEF DESCRIPTION OF THE DRAWINGS

The present invention is further illustrated by the following detailed description set forth in view of the appended drawings, which represent an exemplary and explanatory embodiment of an encoded microcarrier not restrictive of the invention, wherein.

DETAILED DESCRIPTION OF THE INVENTION

Figure 1:
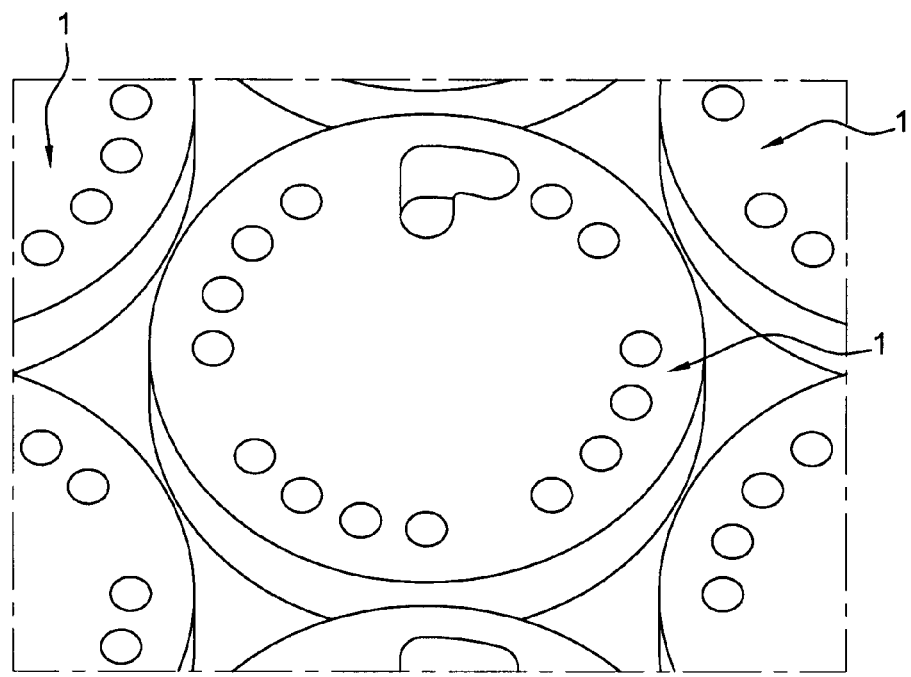
FIG. 1 illustrates a top perspective view of encoded microparticles of the prior art.

An encoded microcarrier 2 of the invention, shown in FIGS. 2, 4, 5 and 6b, comprises a body 3 having a shape of a right circular cylinder delineated by a cylindrical surface 4 and two circular major surfaces 5, as shown in FIGS. 2, 4, 5 and 6b). At least one of these major surfaces 5 comprises a substantially flat detection surface 6, shown on pictures 2 and 5, to detect a chemical and/or biological reaction. A typical diameter of the encoded microcarrier 2 range from 1 to about 200 µm.

The body 3 of said encoded microcarrier 2 has a form of a cylindrical wafer, meaning that the height of the right circular cylinder is notably smaller (by at least a factor two) than the radius of major surfaces 5. In order to be able to detect a chemical and/or biological reaction, the detection surface 6 of the encoded microcarrier 2 is advantageously partially or totally functionalized.

Figure 2:
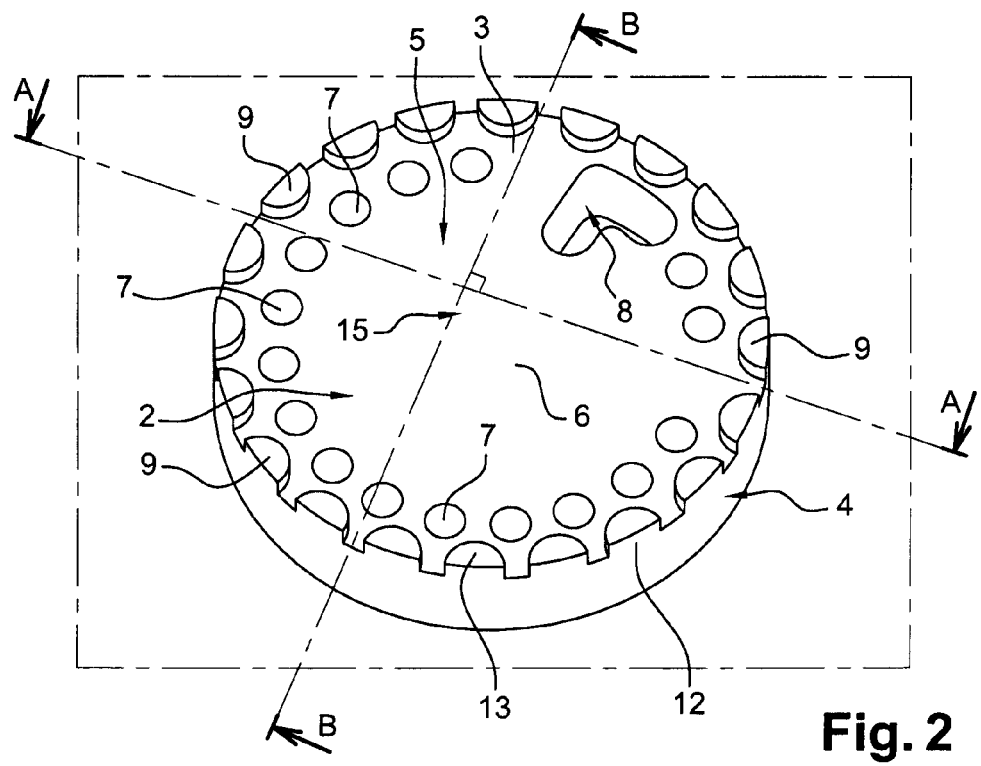
FIG. 2 illustrates a top perspective view of encoded microcarriers according to the invention.

The encoded microcarrier 2 of the invention further comprises a readable code. Thereby, the encoded microcarrier 2 is encoded and functionalized in such a way that its functionalization is determinable by reading its code. As shown in FIGS. 2 and 6b, the code comprises a distinctive pattern of a plurality of traversing holes 7. The code also preferably includes an asymmetric orientation mark 8 such as a L-shaped sign (FIG. 2) or a triangle. This asymmetric orientation mark 8 is meant to distinguish the major surfaces 5 from each other.

An encoded microcarrier 2 according to the invention is made of silicon oxide. An encoded microcarrier 2 of the invention can be shaped using dry and/or wet etching technology.

Figure 5:
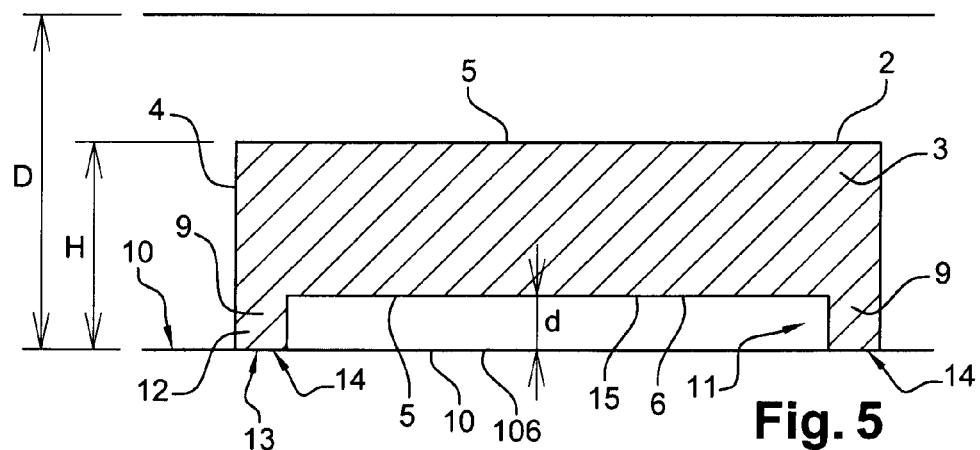
FIG. 5 illustrates a detailed cross-section view of encoded microcarriers of FIG. 2 loaded in the microfluidic channel of FIGS. 3 and 4.

Further, an encoded microcarrier 2 according to the invention comprises a plurality of spacing elements 9, shown in FIGS. 2 and 5, in particular twenty spacing elements 9, projecting from the body 3. The encoded microcarrier 2 with its spacing elements 9 is shaped to ensure that, when the encoded microcarrier 2 is laid on a flat plane 10 with the detection surface 6 facing said plane 10, a gap 11 exists between said flat plane 10 and the detection surface 6, as shown in FIG. 5.

Each spacing element 9 has a shape of a truncated right cylinder 12, is disposed on the periphery of the detection surface 6 and extends in the continuation of the cylindrical surface 4 to a distal end 13. Each circular right cylinder 12 is truncated along its height by the cylindrical surface 4 of the encoded microcarrier 2.

In an alternative, not shown in figures, each spacing element 9 could have a shape of a truncated cone or of a spike.

The heights of each spacing element 9 are equal to each other. The distal ends 13 of each spacing element 9 form together a contacting surface 14, illustrated in FIG. 2, which is substantially parallel to the detection surface 6. When said encoded microcarrier 2 is laid on the flat plane 10 with the detection surface 6 facing such a flat plane 10, this contacting surface 14 is intended to be in contact with said flat plane 10. The size of the contacting surface 14 represents less than 20% of the size of the detection surface 6, preferably less than 15%.

Choosing the height of each truncated right cylinder 12 allows defining the distance d, represented in FIG. 5, between the detection surface 6 and said flat plane 10 on which the encoded microcarrier 2 is laid as described below (FIG. 5). Advantageously, this distance d, i.e. the height of the gap 11, is less than 30% of the greatest height H of the encoded microcarrier 2 (FIG. 5). Most preferably, the distance d is greater than 5% of the height H, more preferably 10%. In the example of the figures, The Height H of the encoded microcarrier 2 is about 10 µm and the distance d is about 1 µm.

The detection surface 6 further has an area 15 wherein, when the encoded microcarrier 2 is laid on the flat plane 10 with the detection surface 6 facing said flat plane 10, each point of said area 15 belongs to the two different cross-sections along the axis AA and BB, shown in FIG. 2, which are perpendicular to each other and to said plane 10. Said cross-sections are free of spacing element 9. This ensures that, when the microcarrier 2 lays flat against said flat plane 10 and is in a laminar flow essentially parallel to that flat plane 10, the orientation of the microcarrier 2 around an axis normal to the flat plane 10 does not significantly affect the flow in the gap 11. In other words, there is no preferred rotational orientation of the microcarrier 2 with regard to the flow, which would change the efficacy of a reaction happening on the detection surface 6.

Functionalized encoded microcarriers 2 are useful to perform chemical and/or biological assays in an assay system according to the invention. Indeed, the encoded microcarrier 2 serves as a support for chemical and/or biological assays. In this capacity, the encoded microcarrier 2 contains one or more ligands bound to its surface, in particular bound to the detection surface 6. When contacting the ligand-bound encoded microcarrier 2 with a solution that may contain one or more target analytes, a reaction of interest may occur on the detection surface 6, depending on the presence or absence of a proper analyte. As an example, a reaction of interest can emit or inhibit of fluorescent signal, which can be monitored. Detecting a reaction on the detection surface 6 can allow determining the presence or absence of particular analytes of interest.

Figure 3:
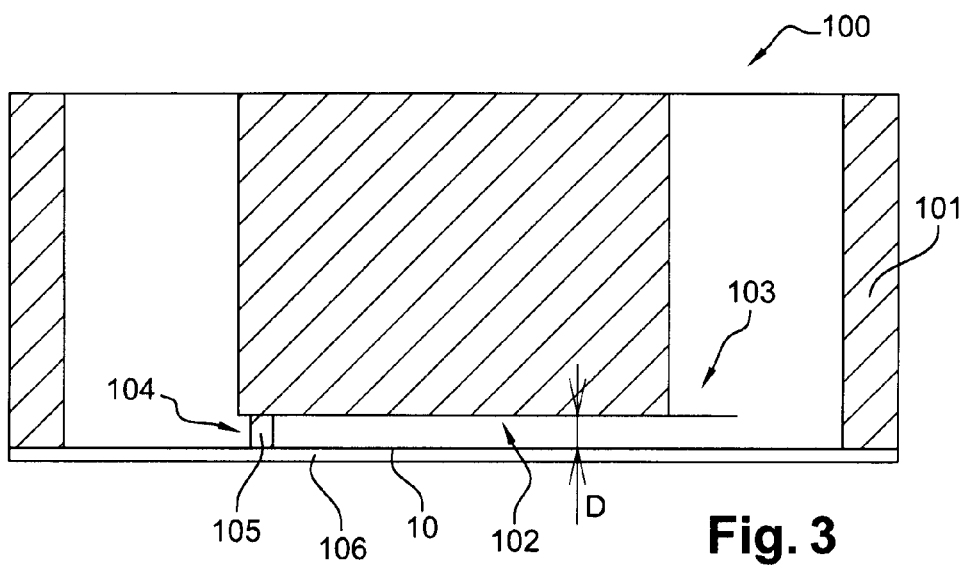
FIG. 3 illustrates a cross-section view of a microfluidic channel of an assay device according to the invention.
Figure 4:
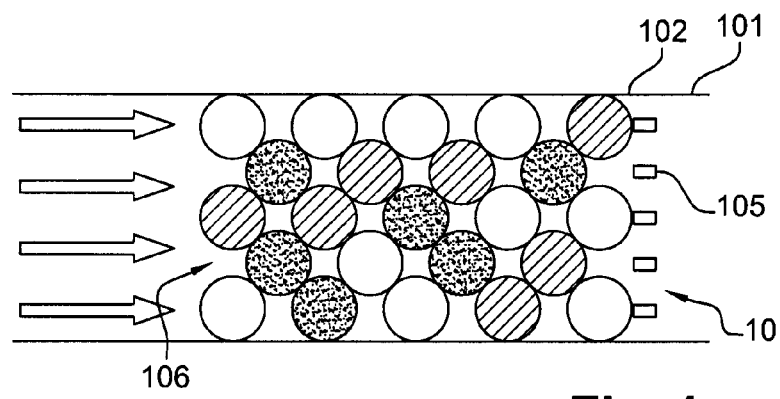
FIG. 4 illustrates a top view of encoded microcarriers of FIG. 2 loaded in the microfluidic channel of FIG. 3.

An assay system 100 according to the invention comprises a plurality of encoded microcarriers 2 of the invention and further comprises an assay device 101, partially shown in FIGS. 3 to 5. The assay device 101 has at least a microfluidic channel 102 depicted in FIGS. 3 to 5. Such an assay device 101 is described for example in the patent application WO 2010/072011, which is herein incorporated by reference in that respect. The microfluidic channel 102 comprises an inlet 103 and an outlet 104 and is shaped to accommodate a plurality of said encoded microcarriers 2. The microfluidic channel 102 is provided with stopping means 105 arranged in the vicinity of the outlet 104 of the microfluidic channel 102 and acting as filters that allow a liquid solution to flow through while blocking said encoded microcarriers 2 Inside. The microfluidic channel 102 has a cross-section that allows at least two encoded microcarriers 2 to be arranged side by side over the length of said microfluidic channel 102, in a monolayer arrangement as depicted in FIG. 4. The size of the microfluidic channel 102 and of the encoded microcarrier 2 are chosen so that the height H of said encoded microcarrier 2 ranges from about 51% to about 95% of the smallest height D (FIG. 5) of the microfluidic channel 102.

The microfluidic channel 102 comprises at least an observation wall 106 through which an assay is monitorable. Typically, when the assay is monitored by fluorescent signal, the observation wall 106 is transparent.

In a system according to the present invention, when the encoded microcarriers 2 are loaded in the microfluidic channel 102 with said detection surface 6 facing said observation wall 106, the spacing elements 9 generate a gap 10 between said detection surface 6 and said observation wall 106 to allow a circulation of liquid in said gap 10. This liquid allowed to flow in the gap 10 contain chemical and/or biological reagent of interest for the assay.

In order to demonstrate the advantage of using encoded microcarriers 2 in the assay system 100 according to the invention instead of using an existing assay system, a set of encoded microparticles 1 of the prior art and a set of encoded microcarriers 2 have been both functionalized with the same ligand, in the same conditions. The chemistry involved in order to functionalize said encoded microcarrier 2 or said encoded microparticle is well known and implies first a silanization of the surface silanol groups followed by an oxidation into carboxyl groups prior to binding a ligand. In the assay described here, the ligand bound on the surfaces was the protein Immunoglobulin G antibody (IgG). The set of encoded microparticles 1 and the set of encoded microcarriers 2 were then each loaded in two similar microfluidic channels 102 and both contacted with the same liquid containing a chemical reagent likely to react with said ligand and to produce a fluorescent signal, which was monitored. For the current assay, the liquid contained an anti-immunoglobulin G (anti-IgG).

Figure 6A:
FIG. 6a illustrates fluorescent emissions on functionalized encoded microparticles of FIG. 1 observed within the first minute of an assay.
Figure 6B:
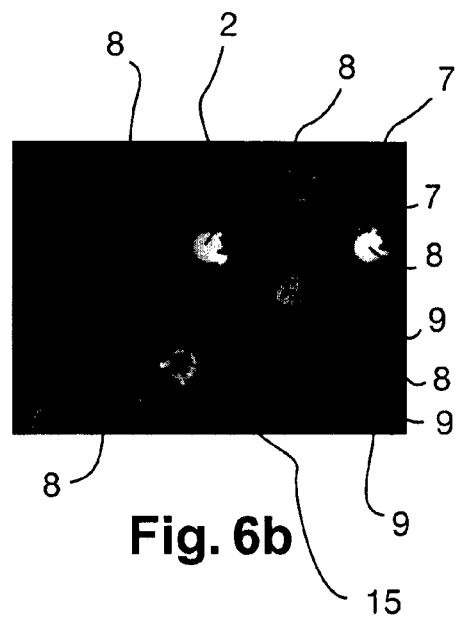
FIG. 6b illustrates fluorescent emissions on encoded microcarriers of FIG. 2 observed within the first minute of an assay.

The FIGS. 6a and 6b show the signal emitted respectively by the encoded microparticles 1 and the encoded microcarriers 2 within the first minute of the assays, at a concentration of about 100 nM.

The surface of a given encoded microparticle 1 of the prior art often shows diffusion pattern or line pattern, as illustrated in FIG. 6a. To the opposite, the encoded microcarriers 2 by the use of the spacing elements 9 exhibit a homogeneous signal on a given detection surface 6, as illustrated in FIG. 6b.

Figure 7A:
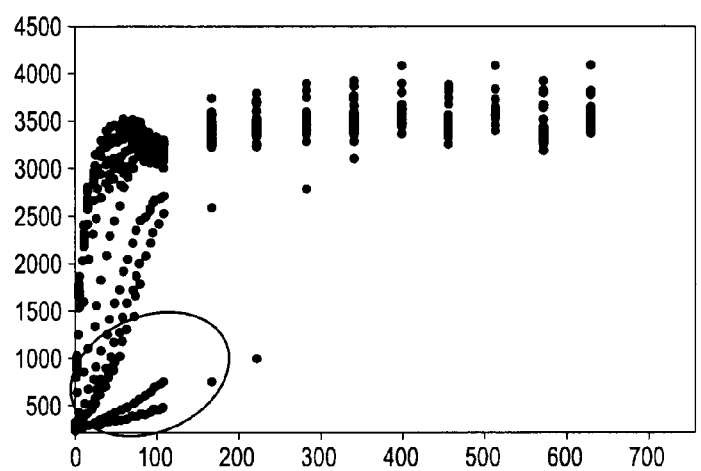
FIG. 7a illustrates the kinetic curves of fluorescent signal occurring on functionalized encoded microparticles of FIG. 1.
Figure 7B:
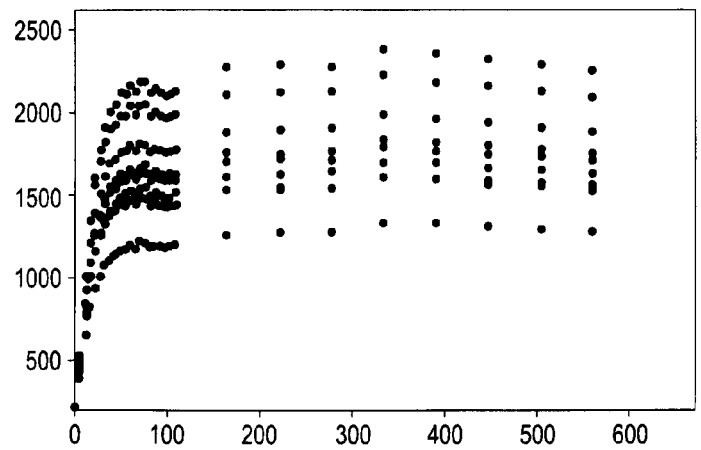
FIG. 7b illustrates a kinetic curves of fluorescent signal occurring on encoded microcarriers of FIG. 2.

The FIGS. 7a and 7b show the quantitative measurements of fluorescent signals respectively for each encoded microparticle 1 or for each microcarrier 2 over the time. The encoded microparticles 1 exhibit significant discrepancies in their fluorescent signals from one microparticle to another, as shown in FIG. 7a, and eventually require a large statistical panel in order to extract significant information.

To the opposite, during the first minutes of an assay, the signals recorded on each detection surfaces 6 of each encoded microcarrier 2 do not exhibit discrepancies with each other, as shown in FIG. 7b.

Thus the spacing elements 9 permit a homogeneous convective flow all over the microfluidic channel 101 resulting in homogeneous fluorescent increase over time and across encoded microcarriers 2.

The homogeneous signal increase allows for a rapid quantification of the analyte being flushed, from the first seconds, by looking at the fluorescence rate. This is not the case with encoded microparticles 1 of the prior art since the fluorescence signal increase is drown in artifacts from mass transfer defect as shown in area emphasized in FIG. 7a, without resorting to a large statistical panel of microparticles.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

Having described the invention, the following is claimed:

1. An encoded microcarrier comprising a readable code for identifying the microcarrier, said microcarrier comprising:
   a body having a detection surface to detect a chemical and/or biological reaction, and
   a plurality of spaced-apart spacing elements projecting outward from a periphery of the body, each spacing element having a distal end, wherein the respective distal ends of the plurality of spacing elements together collectively form a contacting surface that is in a plane substantially parallel to the detection surface, said contacting surface having an area size that is less than 20% of an area size of the detection surface,
   wherein said plurality of spacing elements are shaped such that, when the encoded microcarrier is laid on a flat plane with the detection surface and the contacting surface of the spacing element facing said flat plane, a gap exists between said flat plane and the detection surface.

2. An encoded microcarrier according to claim 1, wherein the area size of said contacting surface is less than 15% of the area size of said detection surface.

3. An encoded microcarrier according to claim 1, wherein said contacting surface is generally planar.

4. An encoded microcarrier according to claim 1, wherein each spacing element is shaped as a truncated cylinder.

5. An encoded microcarrier according to claim 1, wherein the detection surface has at least an area wherein, when said microcarrier is laid on a flat plane with the detection surface facing said flat plane, each point of said area belongs to two different cross-sections of said encoded microcarrier which are perpendicular to each other and to said flat plane, said cross-sections being free of said plurality of spacing elements.

6. An encoded microcarrier according to claim 1, wherein, when the encoded microcarrier is laid on a flat plane with a detection surface facing said flat plane, the greatest distance (d) between said detection surface and said flat plane is greater than 5% of the greatest height (H) between the contacting surface and an upper surface of the encoded microcarrier.

7. An encoded microcarrier according to claim 1, wherein the detection surface is generally planar.

8. An encoded microcarrier according to claim 7, wherein each of said plurality of spacing elements is shaped such that, when the encoded microcarrier is laid on a flat plane with the detection surface facing said flat plane, said flat plane and said detection surface are substantially parallel to each other.

9. An encoded microcarrier according to claim 1, wherein each of said plurality of spacing elements protrudes from the detection surface in a direction generally perpendicular to the detection surface.

10. An encoded microcarrier according to claim 1, wherein said encoded microcarrier comprises at least three spacing elements, said at least three spacing elements face said flat plane when the encoded microcarrier is laid on the flat plane.

11. An encoded microcarrier according to claim 1, wherein each of the plurality of spacing elements is located at the peripheral edge of the encoded microcarrier.

12. An assay system comprising
   a plurality of encoded microcarriers comprising a readable code for identifying the microcarrier, each said microcarrier comprising:
      a body having a detection surface to detect a chemical and/or biological reaction, and
      a plurality of spaced-apart spacing elements projecting outward from a periphery of the body, each spacing element having a distal end, wherein the respective distal ends of the plurality of spacing elements together collectively form a contacting surface that is in a plane substantially parallel to the detection surface, said contacting surface having an area size that is less than 20% of an area size of the detection surface,
   wherein said plurality of spacing elements are shaped such that, when the encoded microcarrier is laid on a flat plane with the detection surface and the contacting surface of the spacing element facing said flat plane, a gap exists between said flat plane and the detection surface,
   an assay device having at least a microfluidic channel shaped to accommodate a plurality of said encoded microcarriers, said microfluidic channel having at least an observation wall through which an assay is monitorable, wherein the spacing elements of each encoded microcarrier are shaped to ensure that, when said encoded microcarrier is introduced in said microfluidic channel with said detection surface facing said observation wall, a gap exists between said detection surface and said observation wall to allow a circulation of fluid in said gap.

13. A method for performing a chemical and/or biological assay comprising a step of using at least an encoded microcarrier comprising a readable code for identifying the microcarrier, said microcarrier comprising:
   a body having a detection surface to detect a chemical and/or biological reaction, and
      a plurality of spaced-apart spacing elements projecting outward from a periphery of the body, each spacing element having a distal end, wherein the respective distal ends of the plurality of spacing elements together collectively form a contacting surface that is in a plane substantially parallel to the detection surface, said contacting surface having an area size that is less than 20% of an area size of the detection surface,
      wherein said plurality of spacing elements are shaped such that, when the encoded microcarrier is laid on a flat plane with the detection surface and the contacting surface of the spacing element facing said flat plane, a gap exists between said flat plane and the detection surface,
   wherein a chemical and/or biological reaction is monitored on the detection surface of said encoded microcarrier.

14. A method according to claim 13, further comprising a step of monitoring the at least one chemical and/or biological reaction through an observation wall of an assay device.

15. A method according to claim 13, further comprising a step of reading the attached code of said encoded microcarrier through an observation wall of an assay device.

* * * * *